(12) United States Patent
Stauffer et al.

(10) Patent No.: US 9,448,208 B2
(45) Date of Patent: Sep. 20, 2016

(54) SYSTEM AND APPARATUS FOR DUAL TRANSDUCER ULTRASONIC TESTING OF PACKAGE SEALS

(71) Applicant: PACKAGING TECHNOLOGIES & INSPECTION LLC, Tuckahoe, NY (US)

(72) Inventors: Anton Stauffer, Tuckahoe, NY (US); Mikhail Kneller, Bronx, NY (US)

(73) Assignee: PACKAGING TECHNOLOGIES & INSPECTION LLC, Tuckahoe, NY (US)

( * ) Notice: Subject to any disclaimer, the term of this patent is extended or adjusted under 35 U.S.C. 154(b) by 287 days.

(21) Appl. No.: 14/249,901

(22) Filed: Apr. 10, 2014

(65) Prior Publication Data
US 2015/0293061 A1    Oct. 15, 2015

(51) Int. Cl.
*G01N 29/04* (2006.01)
*G01N 29/22* (2006.01)
(Continued)

(52) U.S. Cl.
CPC ............ *G01N 29/04* (2013.01); *G01N 29/221* (2013.01); *G01N 29/225* (2013.01); *B29C 65/02* (2013.01); *B29C 65/48* (2013.01); *B29C 65/8292* (2013.01); *B29C 66/112* (2013.01); *B29C 66/1122* (2013.01); *B29C 66/131* (2013.01);
(Continued)

(58) Field of Classification Search
CPC .. G01N 29/04; G01N 29/221; G01N 29/225; G01N 2291/0231; G01N 2291/0289; G01N 2291/048; G01N 2291/057; G01N 2291/105; B29C 65/02; B29C 65/8292; B29C 65/48; B29C 66/112; B29C 66/1122; B29C 66/131; B29C 66/43121; B29C 66/53461; B29L 2031/712
USPC .......................................................... 73/628
See application file for complete search history.

(56) References Cited

U.S. PATENT DOCUMENTS 5,372,042 A  *  12/1994  Jarman ............... G01N 29/0609
                                                                73/588
6,655,114 B2 *  12/2003  Hiramoto ................ B29C 65/18
                                                                53/479
(Continued)

FOREIGN PATENT DOCUMENTS

DE            19852719         6/1999

OTHER PUBLICATIONS

European Search Report and Written Opinion in related European Application No. 15157355.7-1554 dated Aug. 24, 2015.

*Primary Examiner* — J M Saint Surin (57) ABSTRACT

An airborne ultrasonic testing system includes two sets of ultrasound transmitters and receivers, an ultrasound frequency generator, a computer analyzer, and a controller. The ultrasound transmitters and opposing receivers are fixedly mounted at oblique angles from a support. A seal-receiving slot is defined between the transmitters and receivers, and is sized to receive a sealed edge portion of a container to be tested. The ultrasound transmitters preferably emit respective ultrasound streams that encounter a top surface of a sealed edge portion of the container at an angle between approximately 0-45 degrees, and most preferably, approximately 45 degrees. The angle of ultrasound emission of the first transmitter may be inverse of the angle of emission of the second transmitter. The signal response of each pair of receivers can be processed individually or combined to produce a summary test result of the two measurements that eliminates systematic variation associated with material variation.

18 Claims, 7 Drawing Sheets

(51) Int. Cl.
   *B29C 65/82* (2006.01)
   *B29L 31/00* (2006.01)
   *B29C 65/48* (2006.01)
   *B29C 65/00* (2006.01)
   *B29C 65/02* (2006.01)

(52) U.S. Cl.
   CPC .... *B29C66/43121* (2013.01); *B29C 66/53461* (2013.01); *B29L 2031/712* (2013.01); *G01N 2291/0231* (2013.01); *G01N 2291/0289* (2013.01); *G01N 2291/048* (2013.01); *G01N 2291/057* (2013.01); *G01N 2291/105* (2013.01)

(56) References Cited

U.S. PATENT DOCUMENTS

| | | | |
|---|---|---|---|
| 6,840,108 B2 | 1/2005 | Stauffer | |
| 6,920,793 B2 | 7/2005 | Stauffer | |
| 7,036,287 B1* | 5/2006 | Webb | G01N 21/9508 53/53 |
| 7,272,916 B2* | 9/2007 | Webb | G01M 3/38 53/53 |
| 8,201,453 B2* | 6/2012 | Kondo | G01N 29/043 73/600 |
| 2002/0014120 A1 | 2/2002 | Wunderer et al. | |
| 2009/0223295 A1 | 9/2009 | Kondo | |

* cited by examiner

SYSTEM AND APPARATUS FOR DUAL TRANSDUCER ULTRASONIC TESTING OF PACKAGE SEALS

BACKGROUND OF THE INVENTION

1. Field of the Invention

The present invention pertains to the art of testing the integrity of seals associated with various packaging or containers.

2. Discussion of the Prior Art

Figure 1:
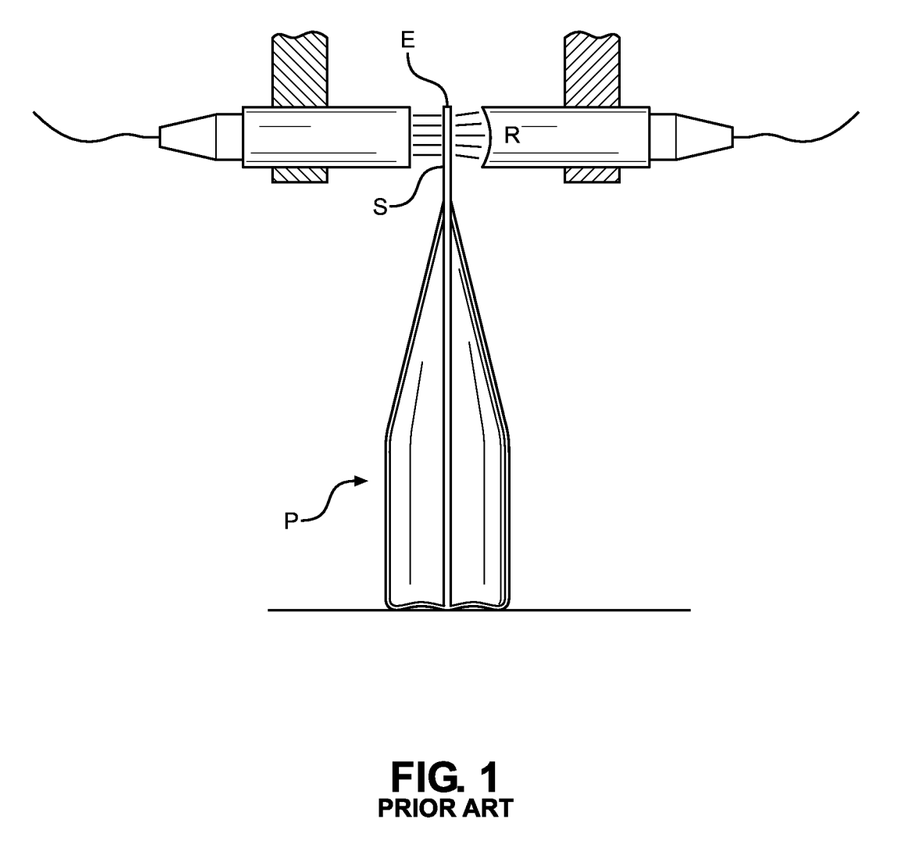
FIG. 1 depicts a prior art ultrasonic testing apparatus.

It is known to provide for airborne ultrasonic testing of packages as set forth in U.S. Pat. Nos. 6,840,108 and 6,920,793 to Stauffer. Stauffer teaches focusing ultrasonic energy from a transmitting transducer, through a package seal, to a receiving transducer. Energy signals passing through the seal are analyzed to provide an indication of seal integrity. FIG. 1 depicts one embodiment of the '108 patent wherein a transducer T directs ultrasonic energy at a receiver R along an axis perpendicular to the length of a seal S of a package P. Care is taken to focus the ultrasonic energy and prevent the ultrasonic energy from extending around the end of the seal E. Advantageously, such a device can be utilized in a gaseous environment, such as under ambient conditions within a product packaging and/or sealing facility. However, there remains a need to optimize and improve package testing while ensuring that any testing method and apparatus is economical so that the cost of packaged products is not increased due to the testing method.

SUMMARY OF THE INVENTION

The present invention is directed to an airborne ultrasonic testing system including a set of ultrasound transmitting transducers, a set of ultrasound receiving transducers, an ultrasound frequency generator, a computer ultrasound energy analyzer, and a computer controller. The ultrasound transmitters are fixedly mounted at an oblique angle from a first arm of a support, while the ultrasound receivers are fixedly mounted at an oblique angle from an opposing arm of the support.

The ultrasound transmitters include respective first and second energy emitting portions positioned offset from corresponding first and second energy receiving portions of the ultrasound receivers. A seal-receiving slot is defined between the ultrasound transmitters and ultrasound receivers, and is sized to receive a sealed edge portion of a package or container to be tested. The ultrasound transmitters preferably emit respective ultrasound streams that each encounter a top surface of a sealed edge portion of a container at an angle between 0-45 degrees. Most preferably, the angle is approximately 45 degrees from perpendicular. In one embodiment, the angle of ultrasound emission of the first transmitter is inverse of the angle of emission of the second transmitter.

In use, a container to be tested is placed in a testing position with a sealed edge portion of the container within the testing slot. The container may be manually positioned, or may be automatically moved into the testing position via a movable support, such as a belt conveyor. Once in the testing position, the frequency generator is actuated and ultrasound energy is transmitted from the transmitters, across the testing slot, through the sealed edge portion, to the receivers. The receivers produce a signal which is passed by way of electrical connection to the computer analyzer to generate ultrasound signal data representative of the seal's quality and/or integrity.

As materials pass through the testing slot, any material irregularity will result in varying quality of signal throughput. The inventors of the present invention have discovered that the optimal angle for signal impact is between approximately 0-45 degrees for maximum signal throughput and detection of seal defects. It has been further discovered that two or more sets of transmitters and receivers can be placed in a similar scanning position targeting the material at inverse angles or at similar angles and offset scanning positions, providing inverse effects of material variation. The signal response of each pair of transducers can be processed individually or combined to produce a summary test result of the two measurements that eliminates systematic variation associated with material variation.

Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF THE PREFERRED EMBODIMENT

Figure 2:
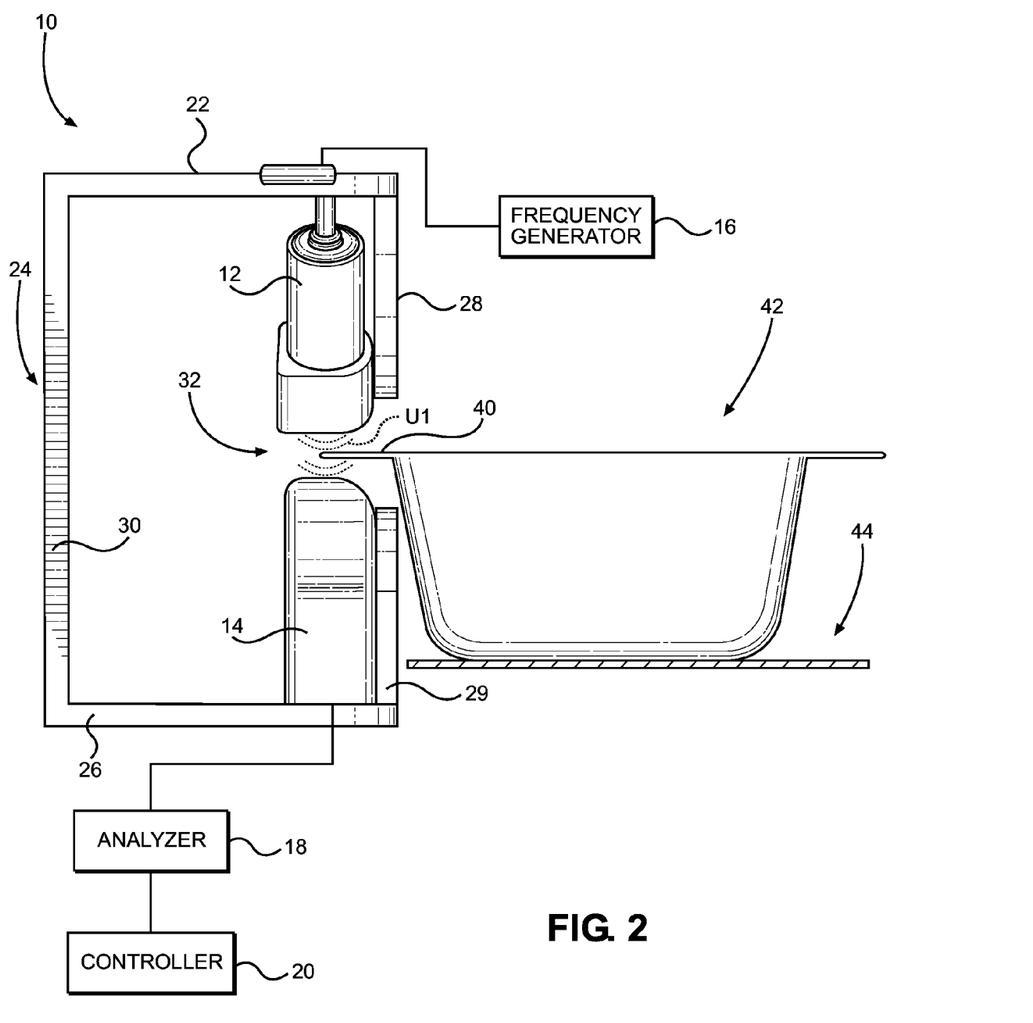
FIG. 2 depicts an ultrasonic dual transducer testing apparatus of the present invention.
Figure 3:
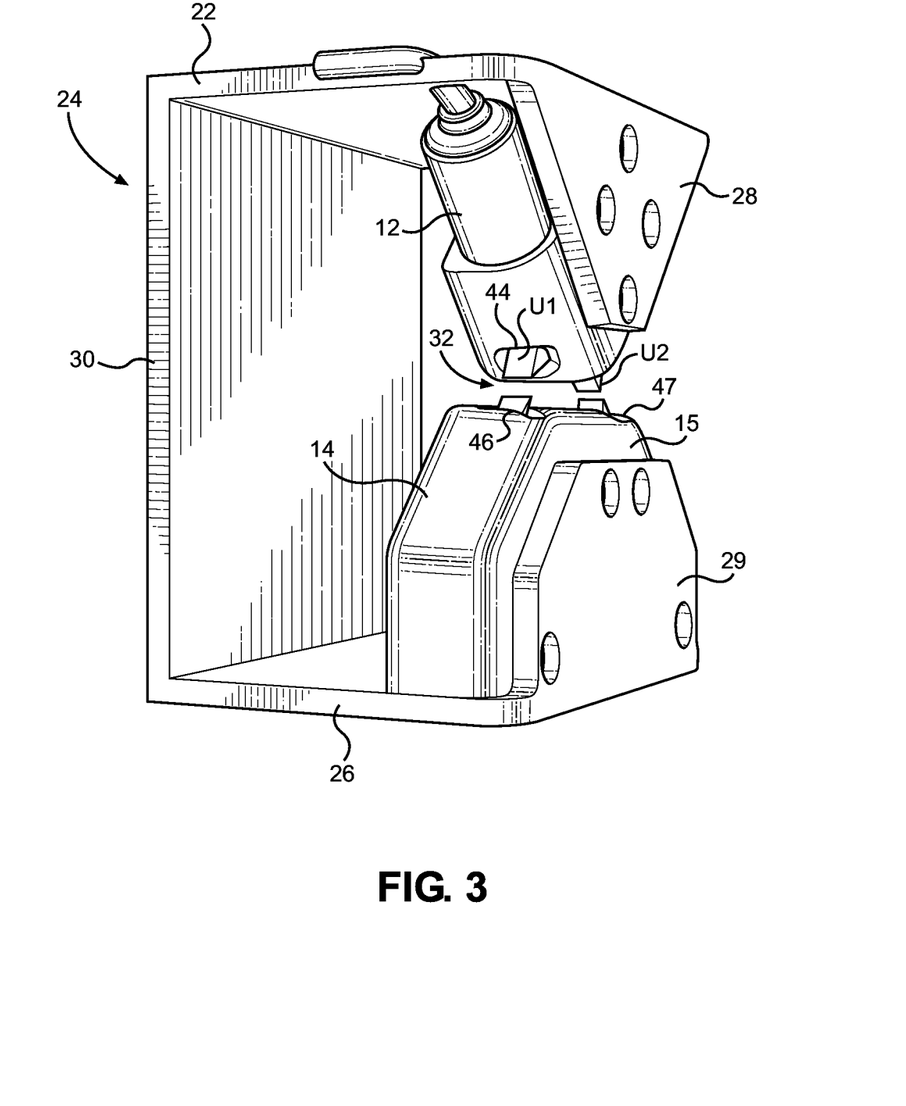
FIG. 3 is a perspective view of dual ultrasonic transducers of the present invention.
Figure 4:
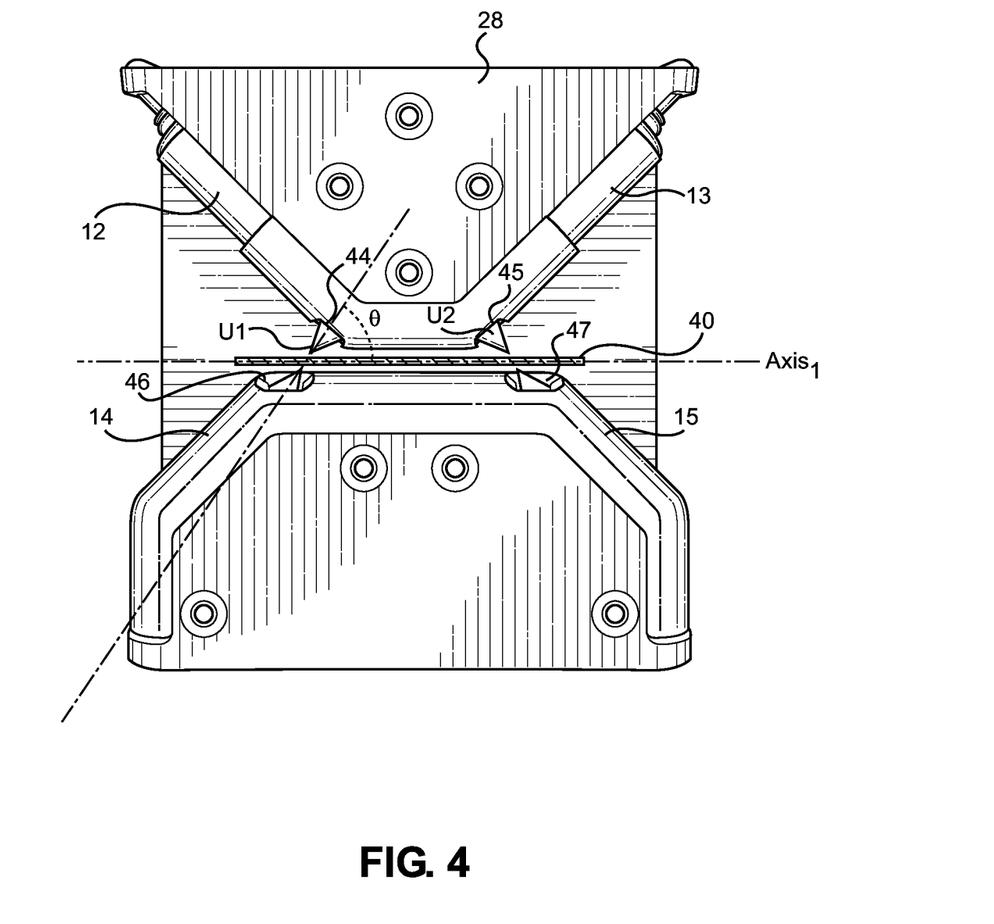
FIG. 4 is a side view of the dual ultrasonic transducers of FIG. 2.

With initial reference to FIGS. 2-4, an ultrasonic dual transducer testing system 10 of the present invention includes a set of ultrasound transmitting transducers or transmitters 12 and 13, a set of ultrasound receiving transducers or receivers 14 and 15, an ultrasound frequency generator depicted at 16, a computer analyzer depicted at 18, and a computer controller 20. Computer analyzer 18 can be any type of standard ultrasound analyzer. Likewise computer controller 20 can be any type of standard computer controller for controlling the actuation of the ultrasound frequency generator 16 during a testing event.

Ultrasound transmitters 12 and 13 are fixedly mounted at an oblique angle from a first support arm 22 of a support 24, while ultrasound receivers 14 are 15 are fixedly mounted at an oblique angle from a second support arm 26 of support 24. In the preferred embodiment shown, first and second flanges 28 and 29 extend at an angle from respective first and second arms 22 and 26 of support 24, and a wall 30 connects first and second support arms 22 and 26, such that support 24 is in the form of a box-like structure. However, it should be understood that the manner in which ultrasound transmitters 12, 13 and receivers 14, 15 can be mounted is not limited to the specific mounting arrangement shown herein.

As best seen in FIGS. 3 and 4, ultrasound transmitters 12,13 include respective first and second exit apertures or energy emitting portions 44 and 45 positioned offset from corresponding first and second apertures or energy receiving portions 46 and 47 of ultrasound receivers 14,15, through which ultrasound energy is received. Ultrasound transmitters 12,13 and ultrasound receivers 14,15 define a testing slot or gap 32 there between sized to receive a sealed edge portion 40 of a package or container 42. Container 42 is positioned on a support 44, which may be a belt conveyor as depicted in FIG. 1. With reference to FIG. 4, ultrasound transmitters 12 and 13 preferably emit respective ultrasound streams U1 and U2 that each encounter a top surface of sealed edge portion 40 of container 42 at an angle of less than 90 degrees. Ultrasound streams U1 and U2 are preferably emitted at an inside angle θ between approximately 0-45 degrees with respect to the longitudinal axis $Axis_1$ of gap 32. Most preferably, the angle θ is approximately 45 degrees from perpendicular.

With this configuration, the present invention enables non-contact airborne ultrasonic testing of containers, whereby the containers do not contact transmitters 12 or receivers 14 during a testing event. It should be understood that container 42 is shown for illustrative purposes only, and system 10 of the present invention may be utilized to test a variety of different product packaging including flexible pouches, formed trays, cups, blister packaging, plastic bottles, Tyvek® containers and the like. Packages or containers which can be inspected utilizing the systems and method of the present invention may be formed of many of a plurality of materials or composites including such materials as plastic films, laminates, papers, metal foils and the like. The seals may be formed by substantially any process including adhesive, welding, heat and pressure sealing and the like.

Methods for utilizing system 10 of the present invention will now be discussed with reference to FIG. 2. Initially, a container 24 to be tested is placed in a testing position with a sealed edge portion 40 within testing gap 32. Container 24 may be manually positioned, or may be automatically moved into the testing position via a movable support 44, such as a belt conveyor. Once in the testing position, frequency generator 16 is actuated and ultrasound energy is transmitted from transmitters 12,13 across testing gap 32, through sealed edge portion 40, to receivers 14,15. The receivers 14, 15 produce a signal which is passed by way of electrical connection to computer analyzer 18.

The inventors of the present invention have discovered that the angle of ultrasonic waves and different surface properties of packages may greatly affect the quality of measurement of system 10. It has been further discovered that the optimal angle for signal impact is between approximately 0-45 degrees for maximum signal throughput and sensitivity. As materials pass through gap 32 between transmitters 12, 13 and receivers 14, 15, any material irregularity will result in varying quality of signal throughput. It has been discovered that two or more sets of transmitters and receivers can be placed in a similar scanning position targeting the material at inverse angles or at similar angles and offset scanning positions, providing inverse effects of material variation. The signal response of each pair of transducers can be processed individually or combined to produce a summary test result of the two measurements that eliminates systematic variation associated with material variation.

Figure 5:
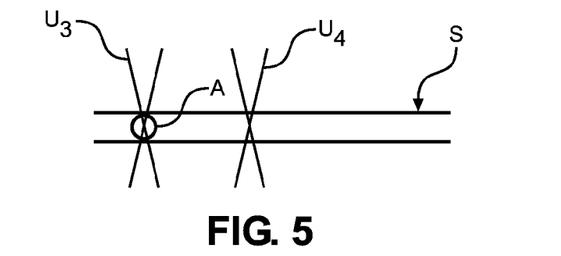
FIG. 5 is a cross-sectional representative view of ultrasonic pulses of the prior art ultrasonic testing apparatus encountering a seal.
Figure 6:
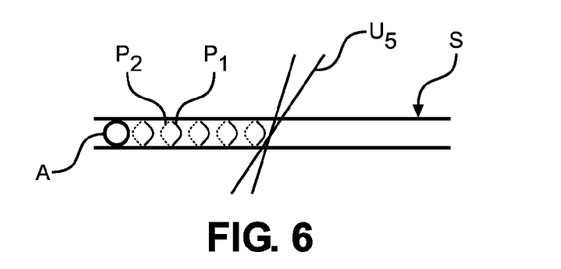
FIG. 6 is a cross-sectional representative view of an ultrasonic pulse of the present ultrasonic testing system encountering a seal.
Figure 7:
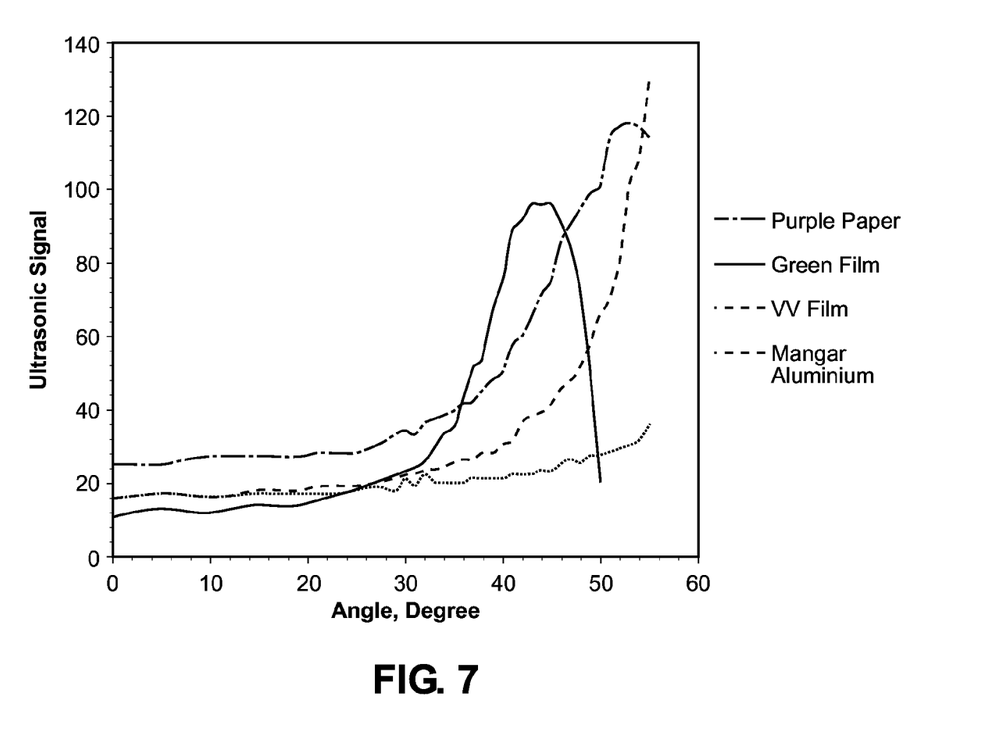
FIG. 7 is a graph depicting ultrasonic signal as a function of angle of incidence for different seal materials.

The benefits of the angled sensing of the present invention will now be discussed in more detail with reference to FIGS. 5-6C. As demonstrated in FIG. 5, the prior art ultrasonic testing system of Stauffer (U.S. Pat. Nos. 6,840,108 and 6,920,793) utilizes ultrasound waves directed along an axis that is perpendicular to the length of a seal S, as depicted in FIG. 1. With reference to FIG. 5, as a seal S moves through a testing gap between an ultrasonic transducer and an ultrasonic receiver, the system of Stauffer focuses ultrasonic waves directed at a portion of the seal S at 90 degrees to the transducer. Therefore, ultrasound waves U4 will impact seal S at the site of an anomaly A when the seal S is directly below the transceiver, but as the associated package moves, subsequent ultrasound waves indicated by U4 will not contact the anomaly A. In contrast, the inventors of the present system have discovered that by angling the ultrasonic transducers 12, 13 and receivers 14, 15 such that ultrasound waves are directed at a seal S at an oblique angle, an eco-effect or bounce back effect is achieved which can provide more detailed information regarding any seal anomaly A. That is, ultrasound waves travel not only perpendicular through the seal, but parallel to the length of the seal as well. For example, FIG. 6 depicts an angled ultrasonic wave impact cite $U_5$. The angle of impact of $U_5$ creates initial pulse waves $P_1$ that travel down the length of seal S. If initial pulse waves $P_1$ encounter an anomaly A, pulse bounce back waves $P_2$ will be created that travel back along the length of seal S. These bounce back waves $P_2$ are detected and contribute to a more accurate reading of the seal S. Waves P1 and P2 are depicted as traveling in a straight line along the length of seal S for illustrative purposes only, and it should be realized that waves can travel and bounce at different angles along the length of seal S. Importantly, the feedback from traveling waves adds to the overall quality of the signal detection. FIG. 7 is a graphical representation of optimal angles of ultrasonic pulses for varying packaging materials. It can be seen that a significant increase in signal strength is realized with the angled sensors of the present invention.

Figure 8A:
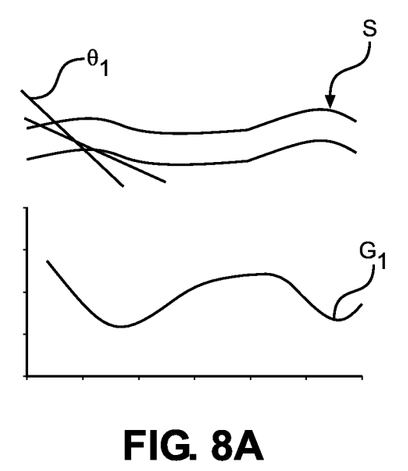
FIG. 8A depicts a measurement graph $G_1$ generated by a signal from a first angled ultrasonic transducer and receiver pair with ultrasound waves impacting seal S at an angle $\theta_1$.
Figure 8B:
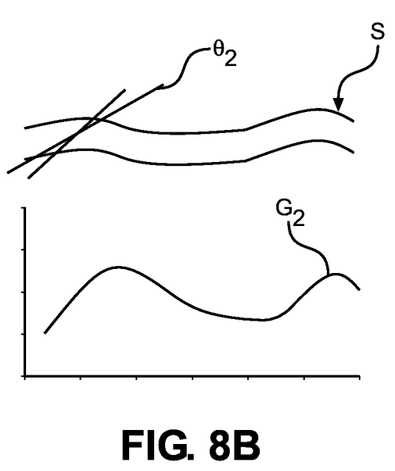
FIG. 8B depicts a measurement graph $G_2$ generated by a signal from a second ultrasonic transducer and receiver pair with ultrasound waves impacting seal S at an angle $\theta_2$ inverse to $\theta_1$.
Figure 8C:
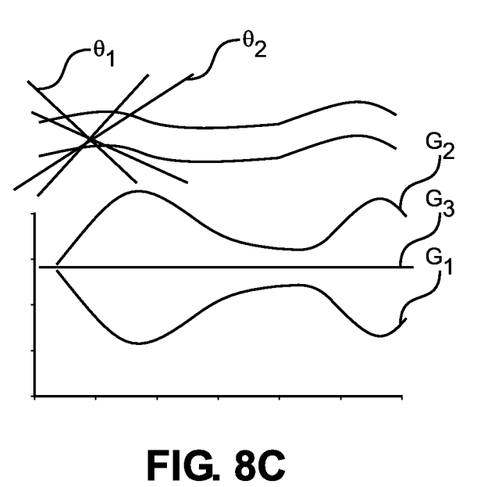
FIG. 8C illustrates how combining two measurements from FIGS. 8A and 8B result in a smooth measurement line $G_3$.

Additionally, it is noted that inverse angle readings can be utilized to eliminate systematic variation association with material variation. For example, FIG. 8A depicts a measurement graph $G_1$ generated by a signal from a first angled ultrasonic transducer and receiver pair with ultrasound waves impacting seal S at an angle $θ_1$. FIG. 8B depicts a measurement graph $G_2$ generated by a signal from a second ultrasonic transducer and receiver pair with ultrasound waves impacting seal S at an angle $θ_2$ inverse to $θ_1$. FIG. 8C illustrates how combining the two measurements results in a smooth measurement line $G_3$.

Figure 9:
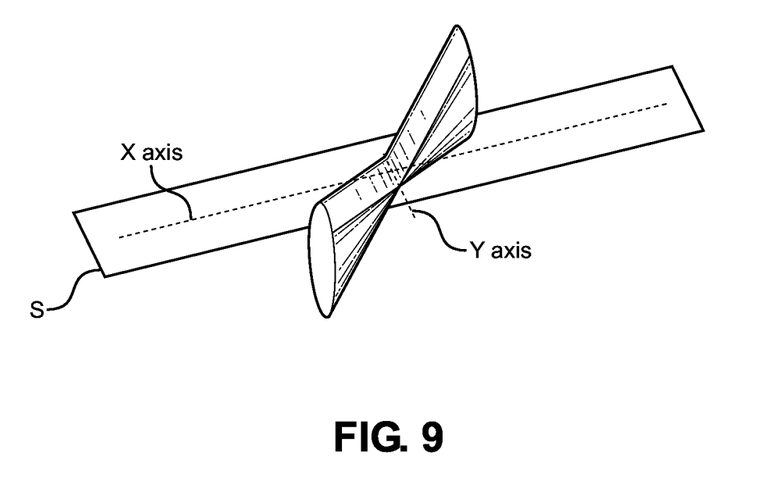
FIG. 9 depicts a line-focused sonic beam embodiment of the present invention.
Figure 10:
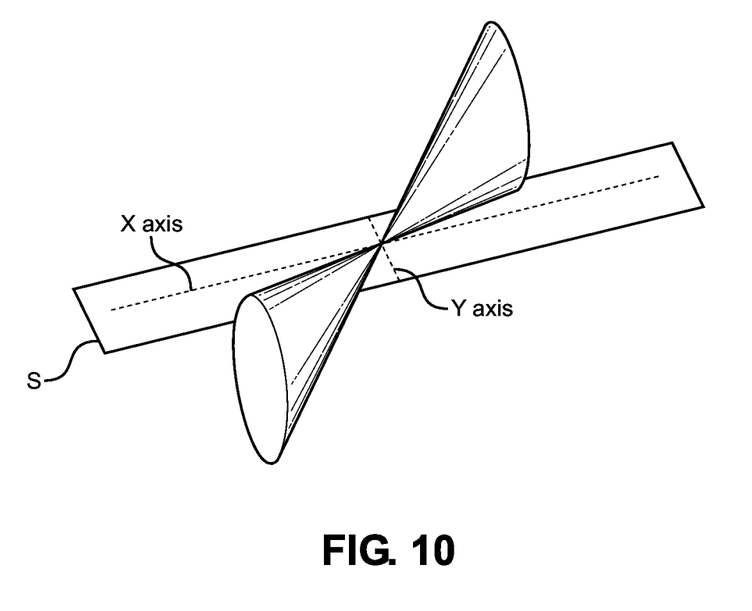
FIG. 10 depicts a point-focused sonic beam embodiment of the present invention.

The present invention may utilized either a "line-focused" sonic beam or a "point focused" sonic beam with a 45 degree central angle. When utilized, the line-focused beam is focused to an elliptical spot of about 4.0×0.7 mm. As depicted in FIG. 9, the beam makes a wedge-like shape with a 45 degree±18 degree angle of incidence on the X-axis (along the seal S on the scanning line) and 0 degrees±10 degrees on the Y axis (across the seal S, in the possible leak direction). Since the Y axis angle is close to perpendicular, Lamb waves are mostly generated on the X-axis. This creates reflection from the left or right edge of the seal that is detectable at about 3 mm from the seal edge. This also creates a strong reflection from any defects (e.g. channels, wrinkles, etc.) oriented across the seal S (parallel to the Y-axis). However, reflection from the top and bottom edge of the seal S is insignificant. Alternatively, the point-focused sonic beam generates a slightly different parabolic reflector, as illustrated in FIG. 10. The point-focused beam focuses most of the sonic energy on a round spot about 0.7 mm in diameter. The point-focused beam makes a cone-shape with a 45 degree±18 degree angle of incidence on the X-axis and 0 degree±18 degree on the Y axis. Unlike the line-focused beam, the point-focused beam creates a significant Lamb waves component across the seal S (on the Y axis). Therefore, the positive effect of energy concentration on a smaller spot is somewhat offset by the negative effect (i.e. noise) of the top or bottom edge of the seal reflection.

Although described with reference to a preferred embodiment of the invention, it should be readily understood that various changes and/or modifications can be made to the invention without departing from the spirit thereof. For instance, although depicted with a conveyor that moves a package in relation to a stationary ultrasonic testing apparatus, the system may instead include a conveyor that moves the ultrasonic testing apparatus in relation to a stationary package. Further, although the means for directing ultrasonic energy at an angle of less than 90 degrees through a seal to be tested is shown as comprising two angled transmitting transducers and two angled receiving transducers offset from the transmitting transducers, it should be understood that reflectors could be utilized to redirect ultrasonic energy at a desired angle with respect to a longitudinal axis of a seal. However, it is noted that such a system would be more complicated an expensive to manufacture, and as such, is not a preferred embodiment. In general, the invention is only intended to be limited by the scope of the following claims.

We claim:

1. An airborne ultrasonic testing apparatus for inspecting a seal of a package in a gaseous environment, comprising:
    a first transmitting transducer having an ultrasound energy emitting portion;
    a first receiving transducer having an ultrasound energy sensing portion;
    a second transmitting transducer having an ultrasound energy emitting portion;
    a second receiving transducer having an ultrasound energy sensing portion;
    a seal-receiving slot defined between the first and second transmitting transducers and the first and second receiving transducers, the seal-receiving slot having a length for receiving therein a seal portion of a package to be tested, wherein the first and second transmitting transducers are configured to emit ultrasound energy towards the respective first and second receiving transducers at an oblique angle with respect to a longitudinal axis of the slot;
    an ultrasound frequency generator in communication with the first and second transmitting transducers;
    a computer analyzer in communication with the first and second receiving transducers, the analyzer providing an indication of integrity of a seal portion of a package to be tested based on a combination of measurements, wherein a measurement from the first receiving transducer is combined with a measurement from the second receiving transducer to eliminate systematic variation and produce a smooth measurement line; and
    a controller in communication with the ultrasound frequency generator for controlling the actuation of the ultrasound frequency generator during a testing event.

2. The airborne ultrasonic testing apparatus of claim 1, wherein each of the ultrasound energy emitting portions of the first and second transmitting transducers is offset from the respective ultrasound energy emitting portions of the first and second transmitting transducers.

3. The airborne ultrasonic testing apparatus of claim 1, wherein the first transmitting transducer emits ultrasound energy at a supplementary angle to the angle of the ultrasound energy emitted by the second transmitting transducer.

4. The airborne ultrasonic testing apparatus of claim 1, wherein the angle of impact of the ultrasound energy with a seal portion of a package to be tested is between approximately 0-45 degrees.

5. The airborne ultrasonic testing apparatus of claim 4, wherein the angle of impact of the ultrasound energy with a seal portion of a package to be tested is approximately 45 degrees.

6. The airborne ultrasonic testing apparatus of claim 1, further comprising:
    a conveyor configured to move a package relative to the first and second transmitting transducers and the first and second receiving transducers during a testing event.

7. The airborne ultrasonic testing apparatus of claim 1, wherein the first and second transmitting transducers emit a line-focused ultrasound beam.

8. The airborne ultrasonic testing apparatus of claim 1, wherein the first and second transmitting transducers emit a point-focused ultrasound beam.

9. A method for airborne ultrasonic testing of a seal of a package in a gaseous environment, the method comprising:
    positioning a seal of a package in a testing position within a seal-receiving slot defined between first and second transmitting transducers and first and second receiving transducers of an ultrasonic testing apparatus, wherein the first and second transmitting transducers are configured to emit ultrasound energy towards the respective first and second receiving transducers at an angle with respect to a longitudinal axis of the slot;
    utilizing a controller to actuate an ultrasound frequency generator in communication with the first and second transducers to selectively emit ultrasound energy;
    utilizing a computer analyzer in communication with the first and second receiving transducers, analyzing information provided by the first and second receiving transducers to provide an indication of integrity of the seal of the package based on a combination of measurements, wherein a measurement from the first receiving transducer is combined with a measurement from the second transducer to eliminate systematic variation and produce a smooth measurement line.

10. The method of claim 9, wherein the first and second transmitting transducers have respective ultrasound energy emitting portions that are offset from respective ultrasound energy sensing portions of the first and second receiving transducers.

11. The method of claim 9, wherein the first transmitting transducer emits ultrasound energy at a supplementary angle to the ultrasound energy emitted by the second transmitting transducer.

12. The method of claim 9, wherein the angle of impact of the ultrasound energy with the seal of the package is between approximately 0-45 degrees.

13. The method of claim 12, wherein the angle of impact of the ultrasound energy with a seal portion of a package to be tested is approximately 45 degrees.

14. The method of claim 9, wherein the step of positioning the seal of the package for testing within the seal-receiving slot is accomplished utilizing a conveyor to automatically move the package into the testing position within the seal-receiving slot.

15. An airborne ultrasonic testing apparatus for inspecting a seal of a package in a gaseous environment, comprising:
- means for directing ultrasound energy at an angle of less than 90 degrees with respect to and through a seal to be tested, wherein means for directing ultrasound energy emits first and second ultrasound streams, and the first ultrasound stream is emitted at a supplementary angle to an angle of the second ultrasound stream;
- a seal-receiving slot having a length for receiving therein a seal portion of a package to be tested;
- a computer analyzer providing an indication of integrity of a seal portion of a package to be tested analyzing information provided by the first and second ultrasound stream to provide an indication of integrity of the seal of the package based on a combination of measurements, wherein a measurement from the first ultrasound stream is combined with a measurement from the second ultrasound stream to eliminate systematic variation and produce a smooth measurement line; and
- a controller for controlling ultrasonic energy during a testing event.

16. The airborne ultrasonic testing apparatus of claim 15, wherein the angle of impact of the ultrasonic energy with a seal portion of a package to be tested is between approximately 0-45 degrees.

17. The airborne ultrasonic testing apparatus of claim 16, wherein the angle of impact of the ultrasonic energy with a seal portion of a package to be tested is approximately 45 degrees.

18. The airborne ultrasonic testing apparatus of claim 15, further comprising:
- a conveyor configured to move a package relative to the means for directing ultrasound energy during a testing event.

* * * * *